United States Patent [19]

Gaffney et al.

[11] 4,454,342

[45] Jun. 12, 1984

[54] PREPARATION OF DIALKYL OXALATES USING A HETEROGENEOUS PD-V-P CATALYST FOR THE OXIDATIVE CARBONYLATION OF ALCOHOLS

[75] Inventors: Anne M. Gaffney; John A. Sofranko, West Chester, Pa.

[73] Assignee: Atlantic Richfield Company, Los Angeles, Calif.

[21] Appl. No.: 397,752

[22] Filed: Jul. 13, 1982

[51] Int. Cl.$^3$ .............................................. C07C 67/36
[52] U.S. Cl. ................................... 560/204; 560/190; 560/193; 502/209
[58] Field of Search .................... 560/204, 193, 190; 252/437, 456, 460, 461, 472

[56] References Cited

U.S. PATENT DOCUMENTS

| | | | |
|---|---|---|---|
| 3,393,136 | 7/1968 | Fenton et al. | 560/204 X |
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,005,130 | 1/1977 | Zehner | 560/204 |
| 4,076,949 | 2/1978 | Zehner | 560/204 |
| 4,118,589 | 10/1978 | Cassar et al. | 560/204 |
| 4,138,587 | 2/1979 | Yamasaki et al. | 560/204 |
| 4,229,591 | 10/1980 | Nishimura et al. | 560/204 |
| 4,230,881 | 10/1980 | Romano et al. | 560/204 |
| 4,281,174 | 7/1981 | Current | 560/204 |

FOREIGN PATENT DOCUMENTS

| | | |
|---|---|---|
| 2213435 | 10/1973 | Fed. Rep. of Germany . |
| 2514685 | 10/1975 | Fed. Rep. of Germany . |
| 50-157311 | 12/1975 | Japan . |
| 51-29428 | 3/1976 | Japan . |

OTHER PUBLICATIONS

Fenton et al., II, *J. Org. Chem.*, vol. 39, No. 5, (1974), pp. 701–704.

Primary Examiner—Natalie Trousof
Assistant Examiner—Vera C. Clarke
Attorney, Agent, or Firm—Delbert E. McCaslin

[57] ABSTRACT

Synthesis of dialkyl oxalates by the heterogeneous catalyzed oxidative carbonylation of liquid monohydric saturated alcohols of from 1 to 20 carbon atoms with carbon monoxide and oxygen or an oxygen-containing gas in the presence of a catalytic amount of a catalyst comprising palladium or a salt thereof in combination with a single phase crystalline vanadium-phosphorus containing compound consisting of vanadium in an oxide form and an oxide of phosphorus.

15 Claims, No Drawings

PREPARATION OF DIALKYL OXALATES USING A HETEROGENEOUS PD-V-P CATALYST FOR THE OXIDATIVE CARBONYLATION OF ALCOHOLS

BACKGROUND OF THE INVENTION

The preparation of dialkyl oxalate esters by the homogeneous catalyzed oxidative carbonylation of alcohols in the presence of metal salt catalysts, redox agents, dehydrating agents and other compounds such as amines, carbonates, nitrates, hydroxides and ureas is well known. An article by Donald M. Fenton and Paul J. Steinwand, Journ. of Org. Chem., Vol. 39, Nos. 5, 1974, pp. 701-704 describes a general mechanism for the oxidative carbonylation of alcohols to yield dialkyl oxalates using a palladium redox system, oxygen and dehydrating agents. Typical prior art patents disclosing homogeneous catalyzed oxidative carbonylation of alcohols to prepare oxalate esters are U.S. Pat. Nos. 3,393,136; 3,994,960; 4,005,129; 4,005,130; 4,076,949; 4,118,589 and 4,281,174 as well as West German Pat. No. 2,213,435 and West German Offenlegungschrift No. 2,601,139.

The present invention provides a much improved process for the production of dialkyl oxalates by employing an insoluble easily recoverable heterogeneous catalyst for the oxidative carbonylation of alcohols.

U.S. Pat. No. 4,229,591 describes a process for the preparation of a diester of oxalic acid by contacting an ester of nitrous acid or an alcohol and a nitrogen oxide or hydrate thereof in the gaseous phase in the presence of a solid catalyst containing palladium or a salt thereof such as palladium on activated carbon.

Japanese Kokai No. 75-157,311 discloses the preparation of oxalic acid esters by reacting a $C_1$ to $C_{20}$ monohydric alcohol, carbon monoxide and molecular oxygen in the presence of a supported Group VIII metal and a Group IB, IIB, III, IV, V, VI, and VIIIB metal, aluminum, iron, cobalt or nickel.

U.S. Pat. No. 4,039,572 discloses the preparation of diesters of dicarboxylic acids by the oxidative carbonylation of olefins and alcohols using a carrier supported catalyst consisting of (1) a platinum group metal compound and (2) a compound of a metal having an atomic number of not less than 22 which has been reduced to a metal and has a ratio of (2) to (1) of from 0.0005:1 to 10:1 gram atoms.

The oxalate products of this invention have many commercial applications and are used as solvents, dye intermediates, for the preparation of pharmaceuticals as well as feedstock for hydrogenation to ethylene glycol by, for example, the process described in U.S. Pat. No. 4,112,245.

SUMMARY OF THE INVENTION

In accordance with the present invention there is provided a superior improved process for the synthesis of dialkyl oxalates by the liquid or vapor phase oxidative carbonylation of a liquid alcohol with a mixture of carbon monoxide and oxygen in the presence of a catalytic amount of an insoluble tri-metallic containing heterogeneous catalyst comprising a combination of (1) palladium metal or a salt thereof and (2) a single phase crystalline vanadiumphosphorus compound consisting of vanadium in oxide form and an oxide of phosphorus. High yield and selectivity of dialkyl oxalates is obtained especially with the lower alcohols. In addition, the Pd-V-P containing catalyst may be supported on, for example silica ($SiO_2$) to provide still greater selectivity and catalyst productivity.

It is a primary object of this invention to provide a process for the preparation of dialkyl oxalates in high yield and high conversion of reactants employing an improved Pd-V-P containing heterogeneous catalyst system.

It is a further object of this invention to provide a specific heterogeneous catalytic mechanism for the employment of palladium or salts thereof with a single phase compound of vanadium in the oxide form and an oxide of phosphorus in an oxidative carbonylation process employing alcohol, carbon monoxide and oxygen as reactants.

These and other objects and advantages of this invention will become apparent from the description of the invention which follows and from the claims.

DESCRIPTION OF THE INVENTION

The present invention is based on the discovery that superior yields of dialkyl oxalates at improved selectivities and catalyst productivity can be obtained from the reaction of an alcohol and a mixture of carbon monoxide, oxygen or an oxygen containing gas, such as air, at elevated temperatures and pressures in the presence of a solid catalytic mixture of palladium or a salt thereof, in combination with a crystalline compound consisting of vanadium in the form of its oxide and an oxide of phosphorus. The Pd-V-P containing catalyst is in the heterogeneous state in the reaction at reaction conditions and while vapor phase reactions employing a bed of catalyst may be employed the reactions are generally carried out with a slurry of the catalyst mixture, supported or unsupported, in the reactant alcohol. The catalyst may be on inert support materials such as alumina, silica gel, aluminosilicates, activated carbon or zeolites, and when so employed will generally provide a higher percent selectivity of product and greater catalyst productivity.

The reaction between the alcohol, carbon monoxide, and oxygen may be carried out in an autoclave or any other high pressure reactor. Although the order of addition of reactants and the Pd-V-P containing catalyst may vary, a general procedure is to charge the alcohol and catalyst (supported or unsupported) into the reaction vessel, and then introduce the proper amount of carbon monoxide and oxygen to the desired reaction pressure and then heat the mixture to the desired temperature for the appropriate period. The reaction can be carried out batchwise or as a continuous process and the order of addition of the reactants may also be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, etc. to effect separation of the oxalate ester from unreacted materials, catalyst, by-products, etc.

The alcohols which may be employed in concentrations of from about 50 to 99.7 weight percent, preferably 77 to 94 weight percent and suitable for use in the process of the present invention can be monohydric saturated aliphatic and alicyclic alcohols and may contain other substitutents such as amido, alkoxy, amino, carboxy, cyano, etc. radicals in addition to the hydroxyl group. The substituents, in general, do not interfere with the reaction.

The alcohols which are employed may be primary, secondary, or tertiary alcohols and conform to the general formula ROH, wherein R is an optionally substituted aliphatic, or alicyclic group containing from 1 to 20 carbon atoms and preferably unsubstituted aliphatic alcohols containing from 1 to 10 carbon atoms and more preferably 1 to 4 carbon atoms. In general, the alcohol is one which is normally liquid under the conditions employed in the carboxylation reaction. Representative alcohols especially suitable for use in this invention are saturated monohydric alcohols such as methyl, ethyl, n-, iso-, sec-, and tert-butyl, amyl, hexyl, octyl, lauryl, n- and iso-propyl, cetyl, benzyl, chlorobenzyl and methoxy-benzyl alcohols as well as for example, cyclohexanol, heptanols, decanols, undecanols, 2-ethyl hexanol, nonanol, myristyl alcohol, stearyl alcohol, methyl cyclohexnol, pentadecanol, oleyl and eicosonyl alcohols, and the like. The preferred alcohols are the primary and secondary monohydric saturated aliphatic alcohols, such as methanol, ethanol, 1- and 2-propanol, n-butyl alcohol etc., up to 10 carbon atoms.

The palladium salts which may be employed in the process of this invention and in forming the catalyst mixture include the palladium (II) compounds or mixtures thereof. Among the chemical forms of the palladium compounds which can be used as such or as mixtures are the palladium, halides, sulfates, carboxylates, acetates, oxides, and nitrates, preferably the palladium (II) halides. Representative palladium salt compounds include, for example palladium (II) oxide, palladium (II) chloride, palladium (II) sulfate, palladium (II) acetate, palladium (II) iodide, palladium (II) oxalate, palladium (II) propionate, etc. The palladium content of the catalyst system may range from about 0.25 to 5 weight percent on the crystalline vanadium oxide-phosphorus oxide compound.

The vanadium employed in the preparation of the crystalline catalyst mixture is in the essentially insoluble oxide form and may be $V_2O_5$, $V_2O_4$ or $V_2O_3$ or mixture thereof as well as pentavalent salts such as ammonium metavanadate.

The oxides of phosphorus employed in the process of this invention and in forming the catalyst mixture include phosphoric acid, phosphorus trioxide (or phosphorus anhydride) $P_4O_6$, phosphorus pentoxide (or phosphoric anhydride) $P_2O_5$ as well as oxides of phosphorus which may be in the form of $P_4O_7$, $P_4O_8$ or $P_4O_9$ or combinations thereof, all of which are generally produced by the direct oxidation of phosphorus. A particularly useful combination of single phase crystalline vanadium-phosphorus which may be employed in the catalyst system is single phase crystalline vanadium-(IV)bis(metaphosphate), $VO(PO_3)_2$ which may be prepared, for example, by the methods described in U.S. Pat. Nos. 4,165,299 and 4,247,419 and incorporated herein by reference or the mixed V-P oxide catalysts of U.S. Pat. No. 4,333,853. The vanadium phosphorus ratio in the crystalline compound will range from about 1:0.5 to about 1:3 and is preferably a ratio of 1:2.

While methods for the preparation of the Pd-V-P supported or unsupported catalyst is set forth hereinafter in the examples, other known methods for the preparation of such catalyst mixture may be used as long as they produce a Pd-V-P catalyst having an appropriate ratio of one metal to the other in the catalyst system. Generally, the atomic ratio of the Pd to V to P as metals in the catalyst employed will range from about 0.01:1:0.5 to about 0.2:1:3 and is preferably 0.05:1:2. The reaction is generally carried out in the presence of a catalytic proportion of the heterogeneous catalyst combination and will proceed with small amounts of the catalyst hereinabove described. Generally the proportions of catalyst used in the reaction as a slurry mixture with alcohol will be equivalent to between about 0.05 to 5 weight percent based on the alcohol employed and is preferably employed in amounts of between 0.5 to 2.5 percent by weight of the alcohol employed.

Although not required, solvents, if desired, which are chemically inert to the components of the reaction system may be employed. Suitable solvents include, for example, hydrocarbons such as hexane, heptane, toluene and xylene; ethers such as tetrahydrofuran, diethylether, diphenylether; halogenated hydrocarbons such as methylene chloride, chlorobenzene and dichlorobenzene; organic esters such as ethyl acetate, n-propyl formate, isopropyl acetate, sec- and iso-butyl acetate, amyl acetate, cyclohexyl acetate, n-propyl benzoate; lower alkyl phthalates, etc. and the alkyl sulfones and sulfoxides such as propylene ethyl sulfoxide, diisopropyl sulfone, diisooctyl sulfoxide, acetone, cyclohexanone, etc.

As indicated above the reaction can be suitably performed by introducing the oxygen and carbon monoxide at a desired pressure into contact with the alcohol/catalyst mixture comprising the palladium-vanadium oxide-phosphorus oxide catalyst either supported or unsupported and heating to the desired temperature. In general, a carbon monoxide pressure of about 400 psig to about 5000 psig partial pressure and preferably from 900 psig to about 2200 psig is employed. Stoichiometric quantities of carbon monoxide are generally employed. However, an excess of carbon monoxide may be employed, for example, in continuous processes where large excess of or high carbon monoxide requirements are generally utilized, a suitable recycle of the unreacted carbon monoxide may be employed. The reaction will proceed at temperatures of from about 40° C. to 150° C. It is generally preferred to operate the process at temperatures in the range of 75° C. to 120° C. to obtain a convenient rate of reaction. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent. The volume percent of the oxygen in the oxygen-carbon monoxide mixture usually amounts to about 3 to 6 percent. In carrying out the reaction the oxygen is charged to the reaction vessel to the desired pressure and concentration and may be charged in portions for safety reasons. Total carbon monoxide-oxygen pressures will range between about 500 psig and 6000 psig.

The reaction time is generally dependent upon the alcohol being reacted, temperature, pressure and on the amount of the catalyst mixture being charged as well as the type of equipment being employed. Reaction times will vary dependent on whether the process is continuous or batch but will generally run for from 0.5 to 2 hours under batch conditions. The reaction is limited by the available oxygen, alcohol and carbon monoxide.

The following examples are provided to illustrate the invention in accordance with the principles of this invention but are not to be construed as limiting the invention in any way except as indicated by the appended claims.

EXAMPLE 1

Preparation of a Pd-V-P Containing Catalyst

A 1 liter, three necked flask equipped with a mechanical stirrer, a condenser with a Dean-Stark water trap, a thermometer and an addition funnel was charged with 60 g. of vanadium pentoxide, 240 ml of isobutyl alcohol and 160 ml of benzyl alcohol. The resulting heterogeneous mixture was stirred at reflux for 4 hours during which time 2 ml of water was collected in the trap. The suspended solids underwent a color change from brown to black indicative of a $V^V$ to $V^{IV}$ reduction. The slurry was then cooled to room temperature and a solution of 91.28 g. of 85 percent ortho-phosphoric acid in 80 ml of isobutanol added slowly over a period of 45 minutes via the addition funnel. A slight exotherm occurred. The resulting mixture was stirred at reflux for 8 hours over which time 15 ml of water was removed. The suspended solids underwent a color change of from black to blue 30 minutes after completion of the phosphoric acid addition. After cooling to room temperature, the solids were collected on a Büchner funnel, washed with 100 ml of isobutanol and air dried for 3 hours. Residual solvents were removed by heating in a vacuum oven at 100° C. for 5 hours. The resulting hard, green solids were ground to a powder and calcined from 100° C. to 400° C. at a rate of 1° C. per minute and then held at 400° C. for 16 hours. The weight of the calcined green crystalline solids equaled 110 g. 19.40 g. of the crystalline vanadium-phosphorus solid material was added to a 35 ml solution of 1N ammonium hydroxide containing 0.999 g. of palladium chloride dissolved therein. The resulting slurry was stirred for 1 hour at room temperature and then heated on a steam bath with stirring to near dryness. After drying at 120° C. for 2 hours, the catalyst was calcined from 100° C. to 400° C. at a rate of 1° C. per minute and then held at 400° C. for 16 hours. The resulting catalyst weight equaled 19.90 g. The atomic ratio of palladium to vanadium to phosphorus as metal in the catalyst was 0.05:1:2.

A $SiO_2$ supported Pd-V-P containing catalyst was prepared in accordance with the above procedure by adding 110 g. of silica gel to the vanadium pentoxide-isobutanol-benzyl alcohol mixture, prior to reflux and addition of the orthophosphoric acid, to give a catalyst containing a palladium to vanadium to phosphorus atomic ratio of 0.066:1:1.2 on silica.

EXAMPLE 2 (Comparative)

To a 500 cc stainless steel stirred autoclave was charged 200 g. of methanol and 2.5 g. of a palladium-vanadium oxide catalyst (1 percent Pd and 56 percent V as the metal). The autoclave was brought to a temperature of 100° C. and 1200 psig of carbon monoxide added with stirring. 400 psig air was charged and then 900 psig carbon monoxide to bring the total pressure to 2500 psig. The reaction was carried out for 1 hour after which the reactor was cooled to ambient temperature and vented to ambient pressure and gas samples obtained. Solids were separated from liquid products by vacuum filtration. The liquid product was analyzed by gas-liquid chromatography (glc) and titration methods and the gaseous product was analyzed by gas chromatograph. Analysis of the products showed 4.86 mmole dimethyl oxalate, 12.6 mmole methyl formate and 0.6 mmole carbon dioxide. Selectivity to dimethyl oxalate was 42.4 percent with a catalyst productivity of 0.573 g/g-hr.

EXAMPLE 3 (Comparative)

The procedure of Example 2 was repeated using 2.5 g. of 2 weight percent palladium metal on silica as catalyst. The reaction was carried out for 1 hour under the same temperature and pressure conditions of Example 2. Analysis of the reaction products showed a selectivity to dimethyl oxalate of 35.7 mole percent with a catalyst productivity of 0.18 g/g-hr.

EXAMPLE 4

To a 500 cc stainless steel stirred autoclave equipped with an internal cooling coil was added a slurry of 200 g. of methanol and 2.5 g. of silica supported Pd-V-P catalyst as prepared by Example 1. While heating the autoclave to 100° C., 1200 psig carbon monoxide followed by 400 psig air and another 900 psig carbon monoxide was added with stirring to bring the total pressure to 2500 psig. The reaction was carried out for 15 minutes after which the reactor was cooled by pumping isopranol cooled in dry ice through the internal coils. A temperature of $-10°$ C. was obtained in 30 minutes. The autoclave was vented to ambient pressure and gas samples obtained. The liquid product was separated from solids by vacuum filtration. The liquid product was analyzed by gas-liquid chromatography (glc) and titration methods and the gaseous product was analyzed by gas chromatograph. Analysis of the products showed 14.2 mmole dimethyl oxalate, 1.2 mmole oxalic acid and 0.6 mmole carbon dioxide. Selectivity to dimethyl oxalate was 95 mole percent with a catalyst productivity of 2.41 g/g-hr.

EXAMPLE 5

The procedure and operating conditions of Example 4 was repeated except that 2.5 g. of unsupported Pd-V-P catalyst as prepared by Example 1 and having a Pd:V:P atomic ratio of 0.05:1:2 was employed. Analysis of the reaction products showed 10.8 mmole dimethyl oxalate, 0.9 mmole oxalic acid and 0.4 mmole carbon dioxide. Selectivity to dimethyl oxalate was 94 mole percent with a catalyst productivity of 2.21 g/g-hr.

EXAMPLES 6 TO 45

In Examples 6 to 45 which follow in table form Table 1, 2, 3 & 4), the procedure of Example 4 was repeated using, 2.5 g. of an unsupported 3 weight percent palladium containing crystalline vanadium-phosphorus catalyst with various V:P atomic ratios, 200 gms. of various alcohol reactants and varying conditions with a 15 minute reaction time. Products were analyzed by gas liquid chromatography and titration methods to give mole percent selectivity to the dialkyl oxalate and catalyst productivity in gram/gram-hour.

TABLE 1

| Example No. | 6 | 7 | 8 | 9 | 10 | 11 | 12 | 13 | 14 | 15 |
|---|---|---|---|---|---|---|---|---|---|---|
| V:P Atomic Ratio | 1:2 | 1:2 | 1:1.2 | 1:1.2 | 1:0.5 | 1:0.5 | 1:2 | 1:2 | 1:1.2 | 1:1.2 |
| Alcohol | MeOH[1] | MeOH | MeOH | MeOH | MeOH | MeOH | MeOH | MeOH | MeOH | MeOH |
| Pressure (psig) | | | | | | | | | | |
| Air | 240 | 480 | 320 | 400 | 320 | 400 | 400 | 400 | 400 | 400 |
| CO | 1260 | 2520 | 1680 | 2100 | 1680 | 2100 | 2100 | 2100 | 2100 | 2100 |
| Temp. (°C.) | 100 | 100 | 100 | 100 | 100 | 100 | 75 | 125 | 75 | 125 |
| Products (mmoles) | | | | | | | | | | |
| Dialkyl Oxalate | 6.8 | 13.9 | 4.1 | 5.4 | 12.5 | 13.1 | 4.0 | 10.2 | 2.0 | 5.1 |
| Oxalic Acid | 0.7 | 2.0 | 0.4 | 0.4 | 1.0 | 4.5 | 0.4 | 1.0 | 0.2 | 0.5 |
| $CO_2$ | 0.3 | 0.5 | 0.8 | 0.8 | 0.7 | 0.7 | 0.4 | 0.5 | 0.8 | 1.0 |
| Selectivity (Mole %) | 93 | 88 | 83 | 87 | 91 | 92 | 84 | 73 | 71 | 66 |
| Catalyst Productivity (g/g-hr.) | 1.41 | 3.0 | 0.85 | 1.10 | 2.56 | 3.33 | 0.84 | 2.12 | 0.42 | 1.06 |

[1] MeOH = Methyl Alcohol

TABLE 2

| Example No. | 16 | 17 | 18 | 19 | 20 | 21 | 22 | 23 | 24 | 25 |
|---|---|---|---|---|---|---|---|---|---|---|
| V:P Atomic Ratio | 1:0.5 | 1:0.5 | 1:2 | 1:2 | 1:2 | 1:1.2 | 1:1.2 | 1:1.2 | 1:0.5 | 1:0.5 |
| Alcohol | MeOH | MeOH | EtOH[2] | PrOH[3] | BuOH[4] | EtOH | PrOH | BuOH | EtOH | PrOH |
| Pressure (psig) | | | | | | | | | | |
| Air | 400 | 400 | 400 | 400 | 400 | 400 | 400 | 400 | 400 | 400 |
| CO | 2100 | 2100 | 2100 | 2100 | 2100 | 2100 | 2100 | 2100 | 2100 | 2100 |
| Temp. (°C.) | 75 | 125 | 100 | 100 | 100 | 100 | 100 | 100 | 100 | 100 |
| Products (mmoles) | | | | | | | | | | |
| Dialkyl Oxalate | 6.1 | 15.9 | 7.8 | 4.0 | 0.9 | 3.9 | 2.0 | 0.5 | 12.0 | 6.0 |
| Oxalic Acid | 0.6 | 1.0 | 0.8 | 0.4 | 0.1 | 0.4 | 0.2 | 0.0 | 1.0 | 0.6 |
| $CO_2$ | 0.7 | 1.2 | 0.4 | 0.5 | 0.6 | 0.8 | 1.0 | 1.5 | 0.8 | 0.7 |
| Selectivity (Mole %) | 82 | 77 | 90 | 75 | 28 | 81 | 59 | 17 | 85 | 70 |
| Catalyst Productivity (g/g-hr.) | 1.27 | 3.20 | 2.01 | 1.22 | 0.33 | 1.00 | 0.61 | 0.17 | 3.03 | 1.83 |

[2] EtOH = Ethyl Alcohol
[3] PrOH = n-Propyl Alcohol
[4] BuOH = n-Butyl Alcohol

TABLE 3

| Example No. | 26 | 27 | 28 | 29 | 30 | 31 | 32 | 33 | 34 | 35 |
|---|---|---|---|---|---|---|---|---|---|---|
| V:P Atomic Ratio | 1:0.5 | 1:2 | 1:2 | 1:1.2 | 1:1.2 | 1:0.5 | 1:0.5 | 1:2 | 1:2 | 1:1.2 |
| Alcohol | BuOH | BuOH | BuOH | BuOH | BuOH | BuOH | BuOH | EtOH | EtOH | EtOH |
| Pressure (psig) | | | | | | | | | | |
| Air | 400 | 400 | 400 | 400 | 400 | 400 | 400 | 400 | 400 | 400 |
| CO | 2100 | 2100 | 2100 | 2100 | 2100 | 2100 | 2100 | 2100 | 2100 | 2100 |
| Temp. (°C.) | 100 | 75 | 125 | 75 | 125 | 75 | 125 | 75 | 125 | 75 |
| Products (mmoles) | | | | | | | | | | |
| Dialkyl Oxalate | 1.4 | 1.3 | 2.2 | 0.7 | 1.2 | 2.0 | 3.4 | 2.9 | 2.3 | 1.5 |
| Oxalic Acid | 0.1 | 0.1 | 0.2 | 0.0 | 0.1 | 0.2 | 0.3 | 0.3 | 0.2 | 0.1 |
| $CO_2$ | 1.2 | 0.2 | 0.8 | 0.5 | 2.0 | 0.4 | 1.6 | 0.1 | 0.9 | 0.2 |
| Selectivity (Mole %) | 26 | 70 | 41 | 50 | 28 | 71 | 40 | 97 | 69 | 89 |
| Catalyst Productivity (g/g-hr.) | 0.50 | 0.46 | 0.79 | 0.24 | 0.41 | 0.70 | 1.20 | 0.74 | 0.60 | 0.37 |

TABLE 4

| Example No. | 36 | 37 | 38 | 39 | 40 | 41 | 42 | 43 | 44 | 45 |
|---|---|---|---|---|---|---|---|---|---|---|
| V:P Atomic Ratio | 1:1.2 | 1:0.5 | 1:0.5 | 1:2 | 1:2 | 1:1.2 | 1:1.2 | 1:0.5 | 1:0.5 | 1:1.2 |
| Alcohol | EtOH | EtOH | EtOH | BuOH | BuOH | BuOH | BuOH | BuOH | BuOH | MeOH |
| Pressure (psig) | | | | | | | | | | |
| Air | 400 | 400 | 400 | 320 | 480 | 320 | 480 | 320 | 480 | 240 |
| CO | 2100 | 2100 | 2100 | 1680 | 2520 | 1680 | 2520 | 1680 | 2520 | 1260 |
| Temp. (°C.) | 125 | 75 | 125 | 100 | 100 | 100 | 100 | 100 | 100 | 100 |
| Products (mmoles) | | | | | | | | | | |
| Dialkyl Oxalate | 1.2 | 4.4 | 3.4 | 1.1 | 2.7 | 0.6 | 1.5 | 1.6 | 4.2 | 3.4 |
| Oxalic Acid | 0.1 | 0.4 | 0.4 | 0.1 | 0.3 | 0.0 | 0.1 | 0.2 | 0.4 | 0.3 |
| $CO_2$ | 1.7 | 0.2 | 1.7 | 0.7 | 0.7 | 1.8 | 1.8 | 1.4 | 1.4 | 0.7 |
| Selectivity (Mole %) | 37 | 96 | 64 | 37 | 58 | 19 | 38 | 34 | 55 | 84 |
| Catalyst Productivity (g/g-hr.) | 0.30 | 1.12 | 0.90 | 0.40 | 0.99 | 0.20 | 0.51 | 0.60 | 1.50 | 0.70 |

We claim:

1. A process for the preparation of dialkyl oxalates by the oxidative carbonylation of a liquid saturated monohydric aliphatic or alicyclic alcohol containing from 1 to 20 carbon atoms with a mixture of carbon monoxide and oxygen or an oxygen containing gas at a temperature of from about 40° C. to 150° C. and a total pressure of between about 500 psig and 6000 psig in the presence of a catalytic amount of an essentially insoluble heterogeneous tri-metallic-containing catalyst comprising palladium or a salt thereof in combination with a single phase crystalline vanadium-phosphorus containing compound consisting of a vanadium oxide and an oxide of phosphorus said catalyst containing as the metals an atomic ratio of palladium to vanadium to phosphorus of from about 0.01:1:0.5 to about 0.2:1:3 and recovering the desired dialkyl oxalate.

2. A process according to claim 1 wherein the alcohol is a monohydric aliphatic alcohol containing from 1 to 10 carbon atoms.

3. A process according to claim 2 wherein the alcohol is selected from the group consisting of methanol, ethanol, propanol and butanol.

4. A process according to claim 3 wherein the alcohol is methanol.

5. A process according to claim 1 wherein the ratio is 0.05:1:2.

6. A process according to claim 1 wherein the vanadium-phosphorus containing crystalline compound has an atomic ratio of V:P of from about 1:0.5 to about 1:3.

7. A process according to claim 6 wherein the ratio is 1:2.

8. A process according to claim 7 wherein the vanadium-phosphorus containing crystalline compound is vanadium(IV)bis(metaphosphate).

9. A process according to claim 1 wherein the Pd-V-P catalyst is employed in amounts of from about 0.05 to 5 weight percent based on the alcohol employed.

10. A process according to claim 9 wherein between 0.5 to 2.5 weight percent catalyst is employed.

11. A process according to claim 1 wherein the temperature is between about 75° C. and 120° C. and carbon monoxide partial pressure is between 900 psig and 2200 psig.

12. A process according to claim 1 wherein the reaction is carried out in a solvent inert to the components of the reaction system.

13. A process according to claim 1 wherein the Pd-V-P containing catalyst is supported.

14. A process according to claim 13 wherein the support is $SiO_2$.

15. A process for the preparation of dimethyl oxalate by the oxidative carbonylation of methanol with carbon monoxide and oxygen or an oxygen-containing gas at a temperature of from 75° C. to 120° C. and a carbon monoxide pressure of 2100 psig and oxygen or oxygen-containing gas pressure of 400 psig in the presence of a catalytic amount of a tri-metallic-containing catalyst comprising palladium or a salt thereof combined with a single phase crystalline vanadium-phosphorus compound consisting of a vanadium oxide and an oxide of phosphorus said catalyst being present in the heterogeneous phase and containing as the metals an atomic ratio of palladium to vanadium to phosphorous of from about 0.01:1:0.5 to about 0.2:1:3.

* * * * *